United States Patent [19]
Meier et al.

[11] 3,931,221

[45] Jan. 6, 1976

[54] PROCESS FOR PREPARING 3-ANILINO-PYRAZOLONES-(5)

[75] Inventors: Ernst Meier; Hans Glockner, both of Munich; Karl Küffner, Unterhaching; Immo Boie; Fritz Nittel, both of Cologne, all of Germany

[73] Assignee: Agfa-Gevaert Aktiengesellschaft, Leverkusen-Bayerwerk, Germany

[22] Filed: Dec. 27, 1973

[21] Appl. No.: 428,670

[30] Foreign Application Priority Data
Jan. 4, 1973   Germany............................ 2300221

[52] U.S. Cl. ........................ 260/310 A; 260/310 R
[51] Int. Cl.² ...................................... C07D 231/20
[58] Field of Search ................................ 260/310 A

[56] References Cited
FOREIGN PATENTS OR APPLICATIONS

| | | |
|---|---|---|
| 1,449,259 | 10/1965 | France |
| 1,469,360 | 2/1966 | France |
| 2,106,154 | 6/1972 | France |
| 2,106,155 | 6/1972 | France |

OTHER PUBLICATIONS
J. Am. Chem. Soc., Vol. 71, pp. 983–988, (1949).

*Primary Examiner*—Donald B. Moyer
*Attorney, Agent, or Firm*—Connolly and Hutz

[57] ABSTRACT

Anilinopyrazolone are to be prepared in high yields and with a high degree of purity by reacting a salt particularly hydrochloride of a $\beta$-arylamino-$\beta$-iminopropionic acid ester of one of the tautomeric formulae which are defined hereinafter with a suitable substituted hydrazine.

5 Claims, No Drawings

PROCESS FOR PREPARING 3-ANILINO-PYRAZOLONES-(5)

This invention relates to a new process for preparing 1-aryl-3-anilino-pyrazolones-(5). These compounds can be used for producing magenta images in color photographic materials by a process of chromogenic development.

The processes described in the Patent literature for preparing these 3-anilino-pyrazolones are not generally applicable. Thus, for example, the method decribed in U.S. Pat. No. 2,343,703 in which amino-pyrazolones react with anilines to liberate ammonia is unsuitable for many aniline derivatives, see German Auslegeschrift No. 1,237,580. This method also fails when certain phenyl hydrazines with electronegative substituents are used, e.g., 2,4,6-trichlorophenyl hydrazine. The improvements of this method which have been described in Russian Pat. No. 141,485 and in Belgian Pat. No. 670,949 also do not give the required result. The method described in German Auslegeschrift No. 1,176,478 in which aryl isocyanates are reacted with sodium acetoacetates is only of limited applicability. Apart from the difficulty of preparing many of the substituted aryl isocyanates, all substituents which react with sodium acetoacetates interfere with the process. The method described in German Auslegeschrift No. 1,237,580 in which malonic ester monoanilides are chlorinated with $PCl_5$ to produce $\beta$-chloro-$\beta$-aryl-aminoacrylic acid esters which are then reacted with aryl hydrazines is restricted to those substitution products which can withstand the treatment with $PCl_5$. Many substituted malonic ester monoanilides resinify when chlorinated with $PCl_5$. The process according to German Auslegeschrift No. 1,101,429, which consists of reacting amidrazones with anilines, has the disadvantage that the preparation of amidrazones is restricted to certain representatives of this class of compounds. Only the methods described in French Pat. Nos. 1,449,259 and 1,469,360, in which $\beta,\beta$-dialkoxyacrylic acid esters or the hydrochlorides of $\beta$-imino-$\beta$-alkoxy acrylic acid esters are reacted with arylamine to produce the corresponding 3-alkoxy-3-aryl-aminoacrylic acid esters are capable of wider application but here again the products are often unsatisfactory in the yields obtained or in their purity on account of their ready solubility. The method described in German Offenlegungsschrift No. 2,042,920 only enables anilinopyrazolones with an acid aniline group to be prepared in high yields whereas in the method described in German Offenlegungsschrift No. 2,042,921 basic anilines can advantageously be combined with hydrazines which have an acidic character to yield anilinopyrazolones. In German Offenlegungsschrift No. 2,015,814, anilinopyrazolones are said to be obtainable in high yields by reacting alkoxy pyrazolones with amine hydrochlorides. However, the preparation of alkoxy pyrazolones described in U.S. Pat. No. 2,439,098 frequently results in unsatisfactory yields, for example the alkoxy pyrazolone of the formula

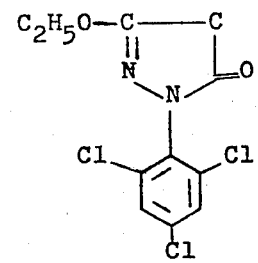

could only be obtained in 40% yield by the process described in U.S. Pat. No. 2,439,098. It is therefore necessary in practice to look for other generally applicable methods of preparing anilinopyrazolones in high yields and particularly with a high degree of purity.

It has now been found that 3-anilino-pyrazolones-(5) of the general formula

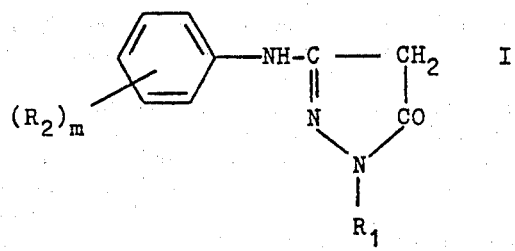

can be prepared by reacting a hydrogenhalogenide salt particularly the hydrochloride of a $\beta$-arylamino-$\beta$-imino-propionic acid ester represented by one of the following tautomeric formulae

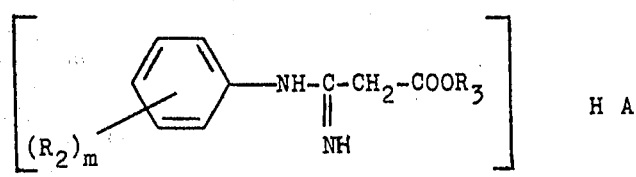

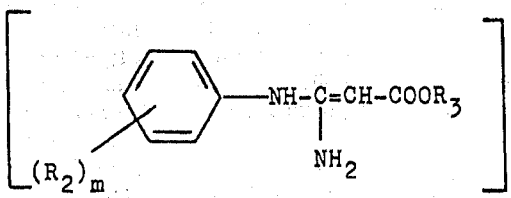

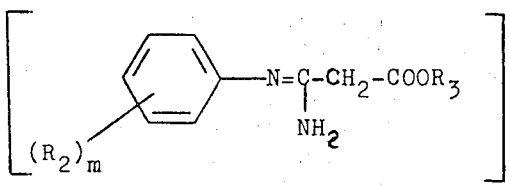

with a hydrazine of the formula

in which
A = Halogen, e.g., Bromine or chlorine
$R_1$ = alkyl, aralkyl, aryl in particular phenyl optionally substituted with one or more alkyl, alkoxy, alkylthio, phenoxy, halogen, carboxy, sulphonic acid, alkylsulphone, arylsulphone, acyl, acylamino, carbaryloxy, carbalkoxy, carbamyl, sulphofluoride trifluoromethyl, sulphamyl, sulphonamide, cyano or nitro groups;
$R_2$ = hydrogen or one or more substituents alike or dissimilar such as
  a. alkyl containing 1 to 20 carbon atoms, alkoxy containing 1 to 20 carbon atoms, alkylthio containing 1 to 20 carbon atoms, halogen, nitro, cyano, trifluoromethyl, carboxyl, sulpho;
  b. carbalkoxy, carbaryloxy, acyl, acylamino, carbamyl, alkyl sulphone, arylsulphone, sulphonamide, sulphamyl, aryl, aralkyl, aryloxy, arylthio or a heterocyclic group
the substituents mentioned under (b) optionally in turn carrying groups, e.g., those mentioned under (a) or (b)
$m$ = an integer of from 1 to 5
$R_3$ = alkyl containing 1 to 4 carbon atoms.

Especially the hydrochlorides of $\beta$-arylamino-$\beta$-imino-propionic acid ethyl esters used according to the invention, which may be in one of the general tautomeric forms represented by formula II above, can be prepared particularly advantageously in a form which is easily purified.

The hydrochlorides of $\beta$-arylamino-$\beta$-imino-propionic acid ethyl esters used according to the invention are isolated in the form of the hydrochlorides by reacting the compound of the general formula

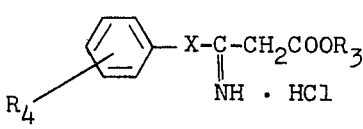

in which
$R_4$ = hydrogen, alkyl, alkoxy or halogen and
X = O or S
with a suitably substituted aniline in accordance with German Pat. application No. AZ P 23 04 587.6. As is well known, hydrochlorides are only sparingly soluble in inert solvents such as ether, petroleum ether or ethyl acetate and are therefore generally easily obtained in a pure crystalline form so that no further purification is required.

With this method, it is possible to prepare 1-aryl-3-anilino-5-pyrazolones which were difficult or even impossible to obtain by the methods previously known. A particular advantage of the method according to the invention is that 3-anilino-pyrazolones which contain a nitro group in the aniline portion can be prepared in particularly high yields. These 3-(nitroanilino)pyrazolones are valuable intermediate products for the preparation of diffusion resistant pyrazolone couplers since after hydrogenation of the nitro group in the anilide portion of the coupler, valuable amino group-containing starting compounds for colour couplers can be made available which can be substituted with any diffusion-preventing groups, for example with acyl, oxacyl or sulphonamide groups.

The following are examples of suitable hydrochlorides of $\beta$-arylamino-$\beta$-imino-propionic acid esters which can be reacted with hydrazines according to the invention:

ethyl $\beta$-anilino-$\beta$-imino-propionate . HCl
ethyl $\beta$-4-chloroanilino-$\beta$-imino-propionate . HCl
ethyl $\beta$-2,4-dichloroanilino-$\beta$-imino-propionate . HCl
ethyl $\beta$-4-nitroanilino-$\beta$-imino-propionate . HCl
ethyl $\beta$-3-nitroanilino-$\beta$-imino-propionate . HCl
ethyl $\beta$-2-chloro-4-nitroanilino-$\beta$-imino-propionate . HCl
ethyl $\beta$-2-chloro-5-nitroanilino-$\beta$-imino-propionate . HCl
ethyl $\beta$-2-methyl-5-nitroanilino-$\beta$-imino-propionate . HCl
ethyl $\beta$-2-methoxy-5-nitroanilino-$\beta$-imino-propionate . HCl
ethyl $\beta$-2-tetradecylthio-5-nitroanilino-$\beta$-imino-propionate . HCl
ethyl $\beta$-3-cyanoanilino-$\beta$-imino-propionate . HCl
ethyl $\beta$-4-carboxyanilino-$\beta$-imino-propionate . HCl
ethyl $\beta$-4-carbomethoxy anilino-$\beta$-imino-propionate . HCl
ethyl $\beta$-4-trifluoromethyl-2-chloroanilino-$\beta$-imino-propionate . HCl
ethyl $\beta$-4-acetaminoanilino-$\beta$-imino-propionate . HCl
ethyl $\beta$-4-sulphaminyl anilino-$\beta$-imino-propionate . HCl
ethyl $\beta$-5-methoxy-2-N,N-diethyl sulphaminyl-anilino-$\beta$-imino-propionate . HCl
ethyl $\beta$-2-chloro-4-(o-tetradecyloxy-carbanilido)-anilino-$\beta$-imino-propionate . HCl
ethyl $\beta$-2-chloro-5-(2'-cyclopentyl-4'-tert.-butyl-phenoxyethoxy-carbamino)-anilino-$\beta$-imino-propionate . HCl.

The following are examples of hydrazines which may be used for the reaction according to the invention: 2,2,2-trifluoroethyl hydrazine, benzyl hydrazine, phenyl hydrazine, m-chlorophenyl hydrazine, p-nitrophenyl hydrazine, 2,4,6-trichlorophenyl hydrazine, 2,6-dichloro-4-methoxy-phenyl hydrazine, 4-hydrazino-methyl-phenyl sulphone, 4-hydrazino-3-chloromethyl-phenyl sulphone, 4-chloro-2-methoxy-phenyl hydrazine, 2,4-dichloro-6-methylphenyl hydrazine. Other suitable hydrazines have been described in Belgian Pat. Nos. 654,108 and 654,110.

The reaction of the hydrochlorides of β-arylamino-β-imino-propionic acid esters according to the invention with a hydrazine is carried out in a solvent such as dioxane, methanol, pyridine or glacial acetic acid or with mixtures thereof at temperatures or between 50°C and 100°C, optionally in the presence of a nitrogen atmosphere.

When methanol is used, the addition of small quantities of glacial acetic acid are particularly advantageous to shorten the reaction time.

The reaction time generally depends on the choice of solvent. When methanol is used with small quantities of glacial acetic acid, the reaction time is between 3 and 6 hours, and when pyridine is used with glacial acetic acid, the reaction time is between 20 and 100 minutes.

If the reaction is carried out with strongly basic hydrazines, the addition of sodium acetate and glacial acetic acid to methanol has the advantage of resulting in higher yields.

It has been found that when phenyl hydrazones which are unsubstituted in the 2- and 6-position are reacted in accordance with the invention, 3-anilino-pyrazolones is directly obtained in glacial acetic acid in high yields and with a high degree of purity. When the reaction according to the invention is carried out with phenyl hydrazones which are disubstituted in the 2- and 6-position, the intermediate compound β-anilino-β-aryl hydrazonopropionic acid ester is first obtained in known manner and this can be cyclized in known manner with alkali metal alcoholate or alkali metal hydroxide to produce the 3-anilino-pyrazolone. In these cases, the reaction according to the invention is preferably carried out in methanol because the intermediate compound in most cases crystallizes in a relatively pure form from methanolic solution.

As already mentioned above, the magenta couplers prepared according to the invention are particularly suitable for producing diffusion-resistant color couplers. They may, of course, also be used directly as such in color photographic materials. The compounds prepared according to the invention and the derivatives prepared from them may be used in the usual color photographic materials.

The following examples serve to illustrate the invention. In examples 1 and 2 it is demonstrated that 3-anilino-pyrazolones can be obtained in higher yields by the process according to the invention than by the process according to French Pat. No. 1,469,360.

EXAMPLE 1

1-(2',4',6'-trichlorophenyl)-3-p-nitroanilinopyrazolone-(5)

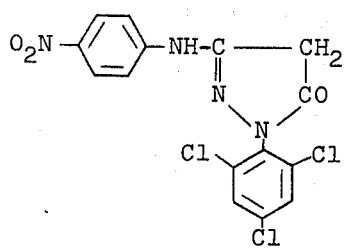

30.2 g (0.105 mol) of ethyl β-4-nitroanilino-β-iminopropionate hydrochloride and 21.2 g (0.1 mol) of 2,4,6-trichlorophenyl hydrazine in 150 ml of methanol and 3 ml of glacial acetic acid were boiled under reflux on a water bath for 3 hours. The hydrazone intermediate product which precipitated in the course of the reaction was suction filtered after cooling. Cyclization of the orange red precipitate was performed by stirring the precipitate with 100 ml of sodium methoxide solution (2.3 g of Na in 100 ml of methanol) for 90 minutes at room temperature. The yellow precipitate obtained after acidification with glacial acetic acid was suction-filtered, washed and dried.

Yield: 25.2 g = 63% of the theory M.p. 300°–302°C.

Example 1 was prepared by the process according to French Pat. No. 1,469,360. The yield obtained was only 53% of the theory.

EXAMPLE 2

1-(2',4',6'-trichlorophenyl)-3-(2''-chloro-5''-nitroanilino)-pyrazolone-(5)

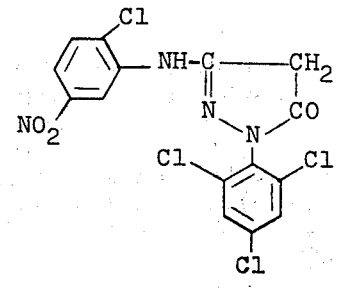

33.8 g (0.105 mol) of ethyl β-2-chloro-5-nitro-anilino-β-imino-propionate hydrochloride and 21.2 g (0.1 mol) of 2,4,6-trichlorophenyl hydrazine in 150 ml of pyridine were stirred at 60°C for 40 minutes. The pyridine solution was poured on to a mixture of 200 ml of glacial acetic acid and 500 ml of ethyl acetate. The product was extracted several times with water to remove glacial acetic acid and pyridine. The ethyl acetate solution was concentrated by evaporation and methanol was added to the residue. The hydrazone intermediate product crystallises from the methanol. Cyclization to the pyrazolone was carried out as described in Example 1. The yield was 25.2 g = 58% of the theory. M.p.: 270°–274°C.

The reaction in methanol according to Example 1 yielded 57% of the theory.

Example 2 was prepared by the process according to French Pat. No. 1,469,360. The yield obtained was only 53 % of the theory.

EXAMPLE 3

1-benzyl-3-(2'-chloro-5'-nitroanilino)-pyrazolone-(5)

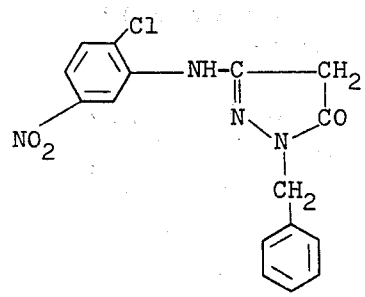

33.8 g (0.105 mol) of the hydrochloride used in Example 2 were boiled under reflux for 2 hours with 12.2 g (0.1 mol) of benzyl hydrazine in 150 ml of methanol with the addition of 20 ml of glacial acetic acid and 8.2 g (0.1 mol) of anhydrous sodium acetate. The precipitated pyrazolone was suction filtered after cooling.

Yield: 15.6 g = 45.5% of the theory M.p.: 232°–234°C.

EXAMPLE 4

1-phenyl-3-(2'-chloro-4-nitroanilino)-pyrazolone-(5)

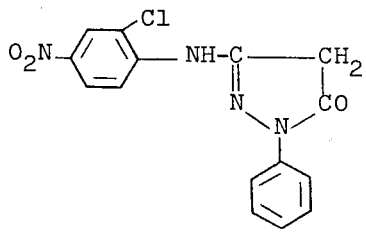

33.8 g (0.105 mol) of ethyl $\beta$-2-chloro-4-nitroanilino-$\beta$-imino-propionate hydrochloride were stirred up with 10.8 g (0.1 mol) of phenyl hydrazine in 50 ml of glacial acetic acid for 60 minutes at a bath temperature of 100°C. A thick crystalline paste was obtained which was suction-filtered when cold and washed with ethyl acetate. Pyrazolone yield: 21 g = 63.5% of the theory. M.p.: 245°–248°C.

EXAMPLE 5

1-(2',4',6'-trichlorophenyl)-3-(2''-chloro-4''-nitroanilino)-pyrazolone-(5)

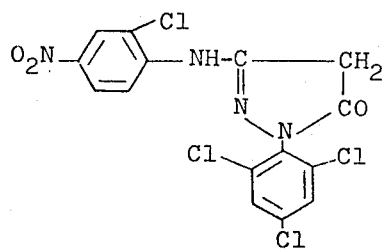

33.8 g (0.105 mol) of ethyl $\beta$-(2-chloro-4-nitroanilino)-$\beta$-imino-propionate-hydrochloride were reacted with 21.2 g (0.1 mol) 2,4,6-trichlorophenyl hydrazine by the method described in Example 1. The pyrazolone is obtained in a yield of 62% of the theory by cyclization. The yield obtained by the process according to French Pat. No. 1,469,360 was only 50% of the theory.

EXAMPLE 6

1-(2,6-dichloro-4-methoxyphenyl)-3-m-nitroanilinopyrazolone-(5)

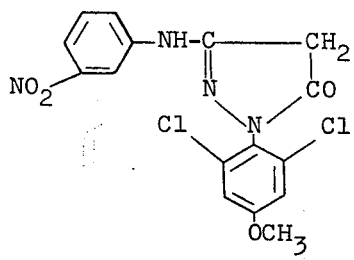

15.1 g (0.0525 mol) of ethyl $\beta$-3-nitroanilino-$\beta$-imino-propionate hydrochloride were reacted with 10.35 g (0.05 mol) 2,6-dichloro-4-methoxyphenyl hydrazine by the method described in Example 1. The yield was 49% of the theory.

EXAMPLE 7

1-m-chlorophenyl-3-(2'-chloro-5'-nitroanilino)-pyrazolone-(5)

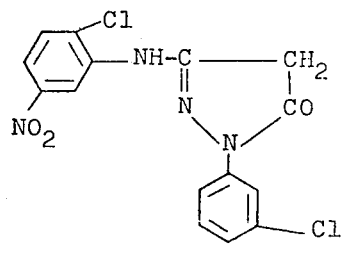

33.8 g (0.105 mol) of ethyl $\beta$-(2-chloro-5-nitroanilino)$\beta$-imino-propionate hydrochloride were reacted with 14.2 g (0.1 mol) of m-chlorophenyl hydrazine by the method described in Example 4. The pyrazolone was obtained immediately in a yield of 61.5% of the theory.

EXAMPLE 8

1-(2',4',6'-trichlorophenyl)-3-(2'',4''-dichloroanilino)-pyrazolone-(5)

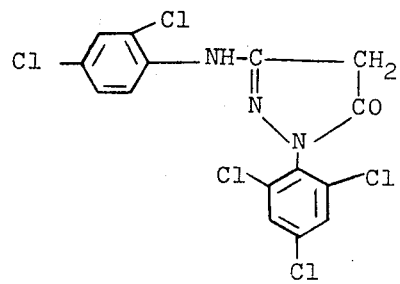

32.7 g (0.105 mol) of ethyl $\beta$-2,4-dichloroanilino-$\beta$-imino-propionate hydrochloride were reacted with 21.2 g of 2,4,6-trichlorophenyl hydrazine by the method described in Example 1. The yield was 50% of the theory.

EXAMPLE 9

1-(2',4',6'-trichlorophenyl)-3-(2''-tetradecylthio-5''-nitroanilino)-pyrazolone-(5)

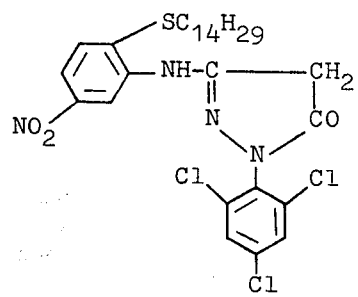

54.2 g (0.105 mol) of ethyl β-(2-tetradecylthio-5-nitroanilino)-β-imino propionate hydrochloride were reacted with 21.2 g (0.1 mol) of 2,4,6-trichlorophenyl hydrazine by the method described in Example 2. The yield was 45% of the theory.

EXAMPLE 10

1-(2'-chloro-5'-chloromethyl-sulphonyl-phenyl)-3-m-cyanoanilino pyrazolone-(5)

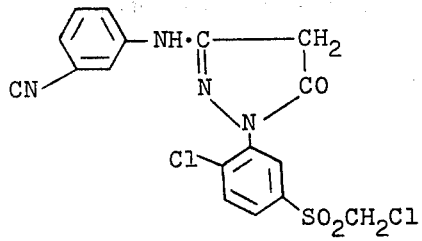

27.8 g (0.105 mol) of ethyl β-cyanoanilino-β-iminopropionate hydrochloride were reacted with 25.5 g (0.1 mol) of 2-chloro-5-chloromethyl-sulphonyl-phenyl-hydrazine by the method described in Example 1.
The yield was 42% of the theory.

EXAMPLE 11

1-(2',4',6'-trichlorophenyl)-3-p-carbomethoxyanilino-pyrazolone-(5)

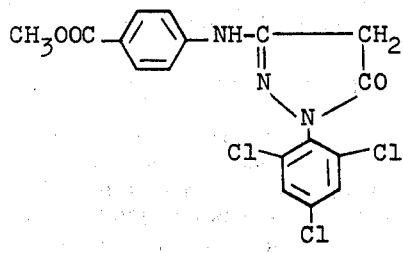

31.5 g (0.105 mol) of ethyl β-4-carbomethoxy anilino-β-imino-propionate hydrochloride were reacted with 21.2 g of 2,4,6-trichlorophenyl hydrazine by the method described in Example 1.
The yield was 38% of the theory.

EXAMPLE 12

1-(2',4',6'-trichlorophenyl)-3-p-carboxy anilinopyrazolone-(5)

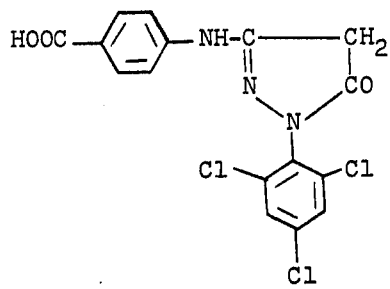

6 g (0.021 mol) of ethyl β-p-carboxy anilino-β-iminopropionate hydrochloride were reacted with 4.2 g (0.2 mol) of 2,4,6-trichlorophenyl hydrazine by the method described in Example 1. The hydrazone intermediate product did not precipitate and was therefore cyclized without being isolated. The pyrazolone precipitated on acidification.
The yield was 48% of the theory.

EXAMPLE 13

1-p-nitrophenyl-3-(2'-trifluoromethyl-4'-chloroanilino)-pyrazolone-(5)

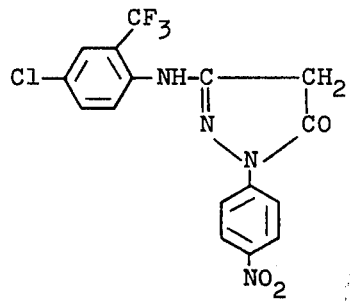

7.3 g (0.021 mol) of ethyl β-(2-trifluoromethyl-4-chloroanilino)-β-imino propionate hydrochloride were reacted with 3.1 g (0.02 mol) of p-nitrophenyl hydrazine by the method described in Example 4. The pyrazolone was formed immediately in a yield of 46% of the theory.

EXAMPLE 14

1-(2',4',6'-trichlorophenyl)-3-(2''-methoxy-5''-N,N-diethyl sulphaminyl-anilino)-pyrazolone-(5)

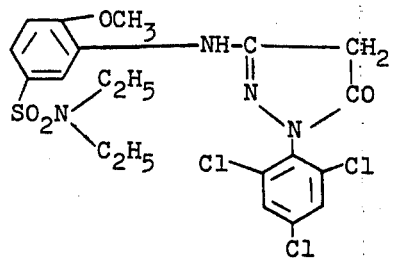

8.6 g (0.021 mol) of ethyl β-(2-methoxy-5-N,N-diethylsulphaminyl-anilino)-β-imino-propionate hydrochloride were reacted with 4.2 g (0.02 mol) of 2,4,6-trichlorophenyl hydrazine by the method described in Example 2.
The yield was 53% of the theory.

EXAMPLE 15

1-(2',4',6'-trichlorophenyl)-3-(2''-chloro-4''-(o-tetradecyloxy-carbanilido)-anilino)-pyrazolone-(5)

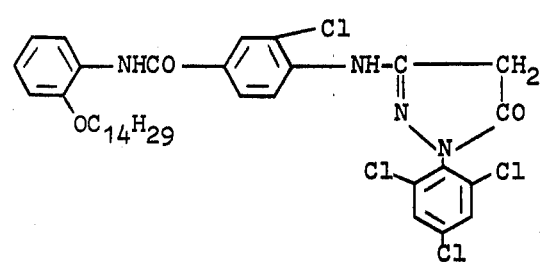

63.9 g (0.105 mol) of ethyl β-(2-chloro-4-(o-tet-radecyloxy)carbanilido-anilino)-β-imino-propionate hydrochloride were reacted with 21.2 g of 2,4,6-trichlorophenyl hydrazine by the method described in Example 1.

The yield was 50% of the theory.

EXAMPLE 16

1-(2',4',6'-trichlorophenyl)-3-(2''-chloro-5''-(β-(2-cyclopentyl-4-tert.-butyl-phenoxy)-ethoxy-carbamino)anilino)-pyrazolone-(5)

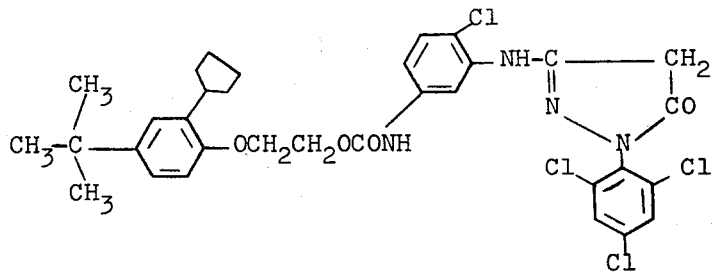

12.2 g (0.021 mol) of ethyl β-2-chloro-5-(2'-cyclopentyl-4'-tert.-butyl-phenoxy-ethoxy carbamino)-anilino-β-iminopropionate . HCl were heated to boiling with 4.23 g (0.02 mol) of 2,4,6-trichlorophenyl hydrazine in 70 ml of dioxane and 1 ml of glacial acetic acid for 2½ hours under nitrogen. After cooling to room temperature, the reaction solution was adjusted to pH 7 with a 4-molar sodium methoxide solution and a further 10 ml were then added. The reaction mixture was stirred for 30 minutes and then poured on to water and acidified. The precipitate was filtered off and dried on a clay brick. The crude product was purified by recrystallisation from 9 : 1 methanol/toluene.

Yield: 6.9 g = 50% of the theory. M.p.: 146°C.

The ethyl β-arylamino-β-imino-propionates used in the above examples were prepared in the form of their hydrochlorides in accordance with Patent application AKZ P 23 04 587.6. The preparation of ethyl β-2-chloro-4-nitroanilino-β-imino-propionate hydrochloride used in Examples 4 and 5 is described in detail below.

First Stage:

ethyl β-phenoxy-β-imino-propionate . HCl 94 g (1 mol) of phenol were dissolved in 113 g (1 mol) of ethyl cyanoacetate. 35.5 g (1 mol) of hydrogen chloride gas were introduced into this solution at −20°C with stirring. The temperature of the reaction mixture was raised to room temperature in the course of 3 hours while a slow stream of hydrogen chloride continued to be passed through. The reaction product solidified in the course of 2 days standing at room temperature. It was stirred up with ether, suction-filtered, washed with petroleum ether and dried in a desiccator.

Yield: 180 g = 74% of the theory.

Second Stage:

ethyl β-2-chloro-5-nitroanilino-β-imino-propionate . HCl 28.6 g (0.11 mol) of ethyl β-phenoxy-β-iminopropionate . HCl and 17.25 g (0.1 mol) of 2-chloro-5-nitroaniline in 80 ml of ethyl acetate were stirred at room temperature for 60 minutes. 100 ml of petroleum ether were then added. The precipitated product was removed and again suspended in ethyl acetate/petroleum ether to free the product from phenol adhering to it.

Yield: 29.0 g = 90% of the theory.

What we claim is:

1. In the process of preparing a 3-anilino-pyrazolone-(5) magenta color coupler by condensing a hydrazine with a hydrohalide of a beta-anilino-acrylic acid ester having in the beta position a second group replaceable by the hydrazine during a pyrazolone-ring-forming cyclization, the improvement according to which the replaceable group is NH$_2$.

2. The combination of claim 1 in which the hydrohalide is the hydrochloride.

3. The combination of claim 1 in which the ester is the ethyl ester.

4. The combination of claim 1 in which the anilino group is nitro-substituted.

5. The combination of claim 1 in which the anilino group is nitro-substituted and the hydrazine is a halogen-substituted aryl hydrazine.

* * * * *